United States Patent [19]

Tomalia et al.

[11] Patent Number: 4,507,466

[45] Date of Patent: Mar. 26, 1985

[54] DENSE STAR POLYMERS HAVING CORE, CORE BRANCHES, TERMINAL GROUPS

[75] Inventors: Donald A. Tomalia, Midland; James R. Dewald, Bay City, both of Mich.

[73] Assignee: The Dow Chemical Corporation, Midland, Mich.

[21] Appl. No.: 456,226

[22] Filed: Jan. 7, 1983

[51] Int. Cl.$^3$ ............................................. C08G 69/00
[52] U.S. Cl. .................................. 528/332; 525/451; 528/310; 528/328; 528/363
[58] Field of Search .............. 528/363, 310, 328, 332, 528/331; 564/153, 155, 468, 509; 560/155, 169, 171, 215; 525/451

[56] References Cited

U.S. PATENT DOCUMENTS

| | | | |
|---|---|---|---|
| 3,528,928 | 9/1970 | Rushton | 252/341 |
| 3,578,643 | 5/1971 | Wood et al. | 528/363 |
| 3,580,891 | 5/1971 | Rainer | 528/310 |
| 3,773,739 | 11/1973 | Bonvicini et al. | 528/310 |
| 4,102,827 | 7/1978 | Rembaum et al. | 260/823 |
| 4,289,872 | 9/1981 | Denkewalter et al. | 528/328 |
| 4,435,548 | 3/1984 | Tomalia et al. | 528/363 |

OTHER PUBLICATIONS

Bauer et al.–Rubber Chem. Tech., 1978, 51(3), pp. 406–436.
Bywater–Adv. Poly. Sci, 30, (1979), pp. 89–116.
Luxton et al.–Polymer, (1978), vol. 19, pp. 1320–1324.
Yen et al.–Poly. Sci. Tech., 2, (1973), pp. 291–312.

*Primary Examiner*—Harold D. Anderson

[57] ABSTRACT

Dense star polymers having terminal group densities greater than conventional star polymers exhibit greater and more uniform reactivity than their corresponding conventional star polymers. For example, a third generation, amine-terminated polyamidoamine dense star polymer prepared from ammonia, methyl acrylate and ethylenediamine has $1.24 \times 10^{-4}$ amine moieties per unit volume (cubic Angstrom units) in contrast to the $1.58 \times 10^{-6}$ amine moieties per unit volume contained by a conventional star polymer. Such dense star polymers are useful as demulsifiers for oil/water emulsions, wet strength agents in the manufacture of paper, and agents for modifying viscosity in aqueous formulations such as paints.

14 Claims, No Drawings

DENSE STAR POLYMERS HAVING CORE, CORE BRANCHES, TERMINAL GROUPS

BACKGROUND OF THE INVENTION

This invention relates to a novel class of branched polymers containing dendritic branches having functional groups uniformly distributed on the periphery of such branches. This invention also relates to processes for preparing such polymers as well as applications therefore.

Organic polymers are generally classified in a structural sense as either linear or branched. In the case of linear polymers, the repeating units (often called mers) are divalent and are connected one to another in a linear sequence. In the case of branched polymers, at least some of the mers possess a valency greater than 2 such that the mers are connected to a nonlinear sequence. The term "branching" usually implies that the individual molecular units of the branches are discrete from the polymer backbone, yet have the same chemical constitution as the polymer backbone. Thus, regularly repeating side groups which are inherent in the monomer structure and/or are of different chemical constitution than the polymer backbone are not considered as branches, e.g., dependent methyl groups of linear polypropylene. To produce a branched polymer, it is necessary to employ an initiator, a monomer, or both that possess at least three moieties that function in the polymerization reaction. Such monomer or initiators are often called polyfunctional. The simplest branched polymers are the chain branched polymers wherein a linear backbone bears one or more essentially linear pendant groups. This simple form of branching, often called comb branching, may be regular wherein the branches are uniformly and regularly distributed on the polymer backbone or irregular wherein the branches are distributed in nonuniform or random fashion on the polymer backbone. See T. A. Orofino, *Polymer*, 2, 295-314 (1961). An example of regular comb branching is a comb branched polystyrene as described by T. Altores et al. in *J. Polymer Sci.*, Part A, Vol. 3, 4131-4151 (1965) and an example of irregular comb branching is illustrated by graft copolymers as described by Sorenson et al. in "Preparative Methods of Polymer Chemistry", 2nd Ed., Interscience Publishers, 213-214 (1968).

Another type of branching is exemplified by cross-linked or network polymers wherein the polymer chains are connected via tetravalent compounds, e.g., polystyrene molecules bridged or cross-linked with divinylbenzene. In this type of branching, many of the individual branches are not linear in that each branch may itself contain groups pendant from a linear chain. More importantly in network branching, each polymer macromolecule (backbone) is cross-linked at two or more sites to two other polymer macromolecules. Also the chemical constitution of the cross-linkages may vary from that of the polymer macromolecules. In this so-called cross-linked or network branched polymer, the various branches or cross-linkages may be structurally similar (called regular cross-linked) or they may be structurally dissimilar (called irregularly cross-linked). An example of regular cross-linked polymers is a ladder-type poly(phenylsilsesquinone) as described by Sorenson et al., supra, at page 390. The foregoing and other types of branched polymers are described by H. G. Elias in *Macromolecules*, Vol. I, Plenum Press, New York (1977).

More recently, there have been developed polymers having so-called star structured branching wherein the individual branches radiate out from a nucleus and there are at least 3 branches per nucleus. Such star branched polymers are illustrated by the polyquaternary compositions described in U.S. Pat. Nos. 4,036,808 and 4,102,827. Star branched polymers prepared from olefins and unsaturated acids are described in U.S. Pat. No. 4,141,847. The star branched polymers offer several advantages over polymers having other types of branching. For example, it is found that the star branched polymers may exhibit higher concentrations of functional groups thus making them more active for their intended purpose. In addition, such star branched polymers are often less sensitive to degradation by shearing which is a very useful property in formulations such as paints, in enhanced oil recovery and other viscosity applications. Additionally, the star branched polymers have relatively low intrinsic viscosities even at high molecular weight.

While the star branched polymers offer many of the aforementioned advantages over polymers having more conventional branching, it is highly desirable to provide polymers which exhibit even greater concentrations of functional groups per unit volume of the polymer macromolecule as well as a more uniform distribution of such functional groups in the exterior regions of the macromolecule. In addition, it is often desirable to provide polymers having macromolecular configurations that are more spheroidal and compact than are the star branched polymers.

SUMMARY OF THE INVENTION

In its broadest aspect, this invention is a dense star polymer having at least one branch (hereinafter called a core branch) emanating from a core, said branch having at least one terminal group provided that (1) the ratio of terminal groups to the core branches is two or greater, (2) the density of terminal groups per unit volume in the polymer is at least 1.5 times that of a conventional star polymer having a comparable molecular weight and number of core branches, each of such branches of the conventional star polymer bearing only one terminal group, and (3) a molecular volume that is equal to or less than about 60 percent of the molecular volume of said conventional star polymer as determined by dimensional studies using scaled Corey-Pauling molecular models.

In a somewhat more limited and preferred aspect, this invention is a polymer having a novel ordered star branched structure (herein called starburst structure). Hereinafter this polymer having a starburst structure in called a dendrimer. Thus, a "dendrimer" is a polymer having a polyvalent core that is covalently bonded to at least two ordered dendritic (tree-like) branches which extend through at least two generations. As an illustration, an ordered second generation dendritic branch is depicted by the following configuration:

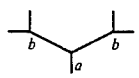

wherein "a" represents the first generation and "b" represents the second generation. An ordered, third generation dendritic branch is depicted by the following configuration.

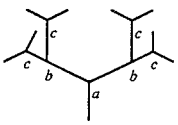

wherein "a" and "b" represent the first and second generation, respectively, and "c" represents the third generation. A primary characteristic of the ordered dendritic branch which distinguishes it from conventional branches of conventional polymers is the uniform or essentially symmetrical character of the branches as is shown in the foregoing illustrations. In addition, with each new generation, the number of terminal groups on the dendritic branch is an exact multiple of the number of terminal groups in the previous generation.

Another aspect of this invention is a process for producing the dense star polymer comprising the steps of
(A) contacting
  (1) a core compound having at least one nucleophilic or one electrophilic moiety (hereinafter referred to in the alternative as N/E moieties) with
  (2) an excess of a first organic coreactant having (a) one moiety (hereinafter called a core reactive moiety) which is reactive with the N/E moieties of the core compound and (b) an N/E moiety which does not react with the N/E moiety of the core under conditions sufficient to form a core adduct wherein each N/E moiety of the core compound has reacted with the core reactive moiety of a different molecule of the first coreactant;
(B) contacting
  (1) the core adduct having at least twice the number of N/E moieties as the core compound with
  (2) an excess of a second organic coreactant having (a) one moiety (hereinafter called an adduct reactive moiety) which will react with the N/E moieties of the core adduct and (b) an N/E moiety which does not react with the N/E moiety of the core adduct under conditions sufficient to form a first generation adduct having a number of N/E moieties that are at least twice the number of N/E moieties in the core adduct; and
(C) contacting the first generation adduct with an excess of a third organic coreactant having one moiety that is reactive with the N/E moieties of the first generation adduct and an N/E moiety that does not react with the N/E moieties of the first generation adduct under conditions sufficient to form a second generation dendrimer. In the foregoing process, the first coreactant differs from the second coreactant, and the second coreactant differs from the third coreactant, but the first and third coreactants may be the same or different compounds. The third and higher generation dendrimers are formed by repeating steps (B) and (C) of the aforementioned process.

Other aspects of this invention are methods for using the dendrimers in such applications as demulsifiers for oil/water emulsions, wet strength agents in the manufacture of paper, agents for modifying viscosity in aqueous formulations such as paints and the like.

The dense star polymers of the present invention exhibit the following properties which are unique or are superior to similar properties of conventional star branched polymers and other branched polymers having similar molecular weight and terminal groups:
(a) greater branch density;
(b) greater terminal group density;
(c) greater accessibility of terminal groups to chemically reactive species; and
(d) lower viscosity.

DETAILED DESCRIPTION OF ILLUSTRATIVE EMBODIMENTS

In the dense star polymers of the present invention, the core is covalently bonded to at least one core branch, preferably at least two, most preferably at least three, core branches with each core branch having a calculated length of at least 3 Angstrom units (A), preferably at least 4 A, most preferably at least 6 A. These polymers preferably have an average of at least 2, more preferably at least 3 and most preferably at least 4 terminal groups per polymer molecule. Preferably, the core branches have a dendritic character, most preferably an ordered dendritic character as defined hereinafter. In preferred dense star polymers, the terminal groups are functional groups that are sufficiently reactive to undergo addition or substitution reactions. Examples of such functional groups include amino, hydroxy, mercapto, carboxy, alkenyl, allyl, vinyl, amido, halo, urea, oxiranyl, aziridinyl, oxazolinyl, imidazolinyl, sulfonato, phosphonato, isocyanato and isothiocyanato. The dense star polymers differ from conventional star or star-branched polymers in that the dense star polymers have a greater concentration of terminal groups per unit of molecular volume than do conventional star polymers having an equivalent number of core branches and an equivalent core branch length. Thus, the density of terminal groups per unit volume in the dense star polymer is at least about 1.5 times the density of terminal groups in the conventional star polymer, preferably at least 5 times, more preferably at least 10 times, most preferably from about 15 to about 50 times. The ratio of terminal groups per core branch in the dense polymer is at least 2, preferably at least 3, most preferably from about 4 to about 1024. Preferably, for a given polymer molecular weight, the molecular volume of the dense star polymer is less than 50 volume percent, more preferably from about 16 to about 50, most preferably from about 7 to about 40 volume percent of the molecular volume of the conventional star polymer.

In the preferred polyamidoamine dense star polymers, the density of terminal (primary) amine moieties in the polymer is readily expressed as the molar ratio of primary amine moieties to the total of secondary and tertiary amine moieties. In such polymers this 1° amine:(2° amino+3° amine) is preferably from about 0.37:1 to about 1:33:1, more preferably from about 0.69:1 to about 1.2:1, most preferably from about 1.1:1 to about 1.2:1.

The preferred dendrimers of the present invention are characterized as having a polyvalent core that is covalently bonded to at least two ordered dendritic branches which extend through at least two generations. Such ordered branching can be illustrated by the following sequence wherein G indicates the number of generations:

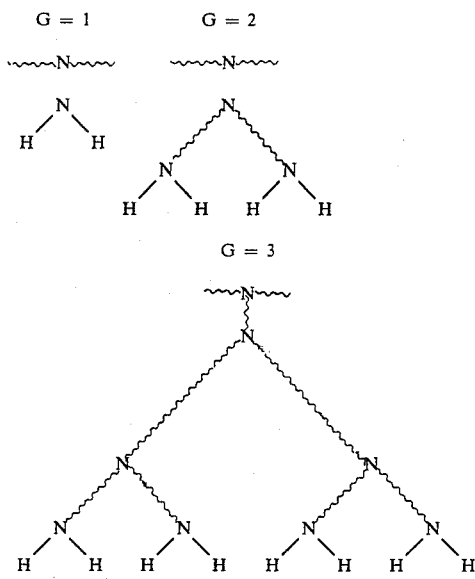

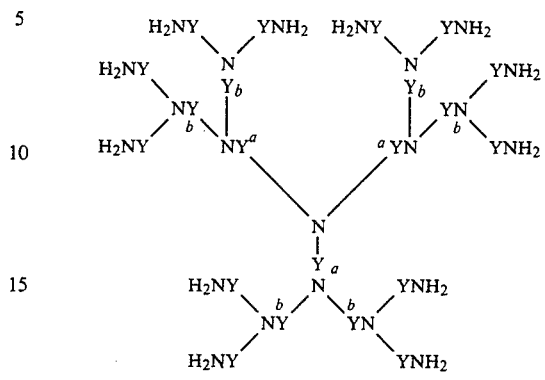

defined hereinbefore. An example of such a ternary dendrimer is polyamidoamine represented by the following structural formula:

wherein Y represents a divalent amide moiety such as $$-CH_2CH_2\overset{O}{\overset{\|}{C}}NHCH_2CH_2-$$

Mathematically, the relationship between the number of terminal groups on a dendritic branch and the number of generations of the branch can be represented as follows:

\# of terminal groups per dendritic branch = $N_r{}^G/2$ wherein G is the number of generations and $N_r$ is the repeating unit multiplicity which is at least 2 as in the case of amines. The total number of terminal groups in the dendrimer is determined by the following:

\# of terminal groups per dendrimer = $N_c N_r{}^G/2$ wherein G and $N_r$ are as defined before and $N_c$ represents the valency (often called core functionality) of the core compound. Accordingly, the dendrimers of the present invention can be represented in its component parts as follows:

$$(\text{Core})\left[(\text{Repeat Unit})_{\frac{N_r{}^G-1}{N_r-1}}\left(\begin{array}{c}\text{Terminal}\\\text{Moiety}\end{array}\right)_{\frac{N_r{}^G}{2}}\right]_{N_c}$$

wherein the Core, Terminal Moiety, G and $N_c$ are as defined before and the Repeat Unit has a valency or functionality of $N_r + 1$ wherein $N_4$ is as defined before.

An illustration of a functionally active dendrimer of a ternary or trivalent core which has three ordered, second generation dendritic branches is depicted by the following configuration:

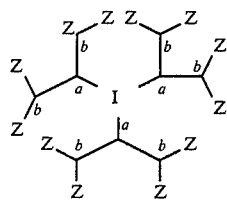

wherein I is a trivalent core atom or molecule having a covalent bond with each of the three dendritic branches, Z is a terminal moiety and "a" and "b" are as and "a" and "b" indicate first and second generations, respectively. In these two illustrations, $N_c$ is 3 and $N_r$ is 2. In the latter of the two illustrations, the Repeat Unit is YN. While the foregoing configuration and formula illustrate a trivalent core, the core atom or molecule may be any monovalent or monofunctional moiety or any polyvalent or polyfunctional moiety, preferably a polyvalent or polyfunctional moiety having from 2 to about 2300 valence bonds of functional sites available for bonding with the dendritic branches, most preferably from about 2 to about 200 valence bonds or functional sites. In cases wherein the core is a monovalent or monofunctional moiety, the dense star has only one core branch and must be compared with a linear polymer in order to determine appropriate terminal group density and molecular volume. Accordingly, this dense star must have at least 2 generations in order to exhibit the desired density of terminal groups. Also, Y may be any other divalent organic moiety such as alkylene, alkylene oxide, alkyleneamine, and the like, with the depicted amide moiety being the most preferred. In addition to amine, the terminal groups of the dendrimer may be any functionally active moiety that can be used to propagate the dendritic branch to the next generation. Examples of such other moieties include carboxy, aziridinyl, oxazolinyl, haloalkyl, oxiranyl, hydroxy and isocyanato, with amine or carboxylic ester moieties being preferred. While the dendrimers preferably have dendritic branches having 2 to 6 generations, dendrimers having dendritic branches up to 12 generations are suitably made and employed in the practice of this invention.

The dendrimers of this invention are readily prepared by reacting a compound capable of generating a polyvalent core with a compound or compounds which causes propagation of dendritic branches from the core. In the preparation of these dendrimers, it is essential to maintain an excess of coreactant to reactive moieties in the terminal groups in the core, core adduct or subsequent adducts and dendrimers in order to prevent cross-linking and to maintain the ordered character of the dendritic branches. In general, this excess of coreactant to reactive moities in the terminal groups is from about 2:1 to about 120:1, preferably from about 3:1 to about 20:1 on a molar basis.

For example in the formation of the aforementioned ternary dendritic polyamidoamine, ammonia, a nucleophilic core compound, is first reacted with methyl acrylate under conditions sufficient to cause the Michael addition of one molecule of the ammonia to three molecules of the methyl acrylate to form the following core adduct:

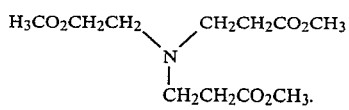

Following removal of unreacted methyl acrylate, this compound is then reacted with excess ethylenediamine under conditions such that one amine group of the ethylenediamine molecule reacts with the methyl carboxylate groups of the core adduct to form a first generation adduct having three amidoamine moieties represented by the formula:

The molar excess of ethylene diamine to methyl acrylate moieties is preferably from 4:1 to 50:1. Following removal of unreacted ethylenediamine, this first generation adduct is then reacted with excess methyl acrylate under Michael's addition conditions to form a second generation adduct having terminal methyl ester moieties:

which is then reacted with excess ethylenediamine under amide forming conditions to produce the desired polyamidoamine dendrimer having ordered, second generation dendritic branches with terminal amine moieties. The molar excess of coreactant to reactive moieties in each case is preferably from 1.1:1 to about 40:1, most preferably from about 3:1 to about 10:1. Similar dendrimers containing amidoamine moieties can be made by using organic amines as the core compound, e.g., ethylenediamine which produces a tetra-branched dendrimer or diethylenetriamine which produces a penta-branched dendrimer.

Alternatively, water or hydrogen sulfide may be employed as nucleophilic cores for the production of binary dendrimers. Examples of other nucleophilic core compounds include phosphine, polyalkylene polyamines such as diethylenetriamine, triethylenetetramine, tetraethylenepentamine and both linear and branched polyethylenimine; primary amines such as methylamine, hydroxyethylamine, octadecylamine and polymethylenediamines such as hexamethylenediamine; polyaminoalkylarenes such as 1,3,5-tris(aminomethyl)-benzene; tris(aminoalkyl)amines such as tris(aminoethyl)amine; heterocyclic amines such as imidazolines and piperidines; and various other amines such as hydroxyethylaminoethylamine, mercaptoethylamine, morpholine, piperzine, amino derivatives of polyvinylbenzyl chloride and other benzylic polyamines such as tris(1,3,5-aminomethyl)benzene. Other suitable nucleophilic cores include ethylene glycol and polyalkylene polyols such as polyethylene glycol and polypropylene glycol; 1,2-dimercaptoethylene and polyalkylene polymercaptans; thiophenols, and phenols. Of the core compounds, ammonia and the polyalkylene polyamines are preferred.

Examples of coreactant materials used to react with the nucleophilic core compounds include $\alpha,\beta$-ethylenically unsaturated carboxylic esters and amides such as methyl acrylate, ethyl acrylate, acrylonitrile, methyl itaconate, dimethyl fumarates, maleic anhydride, acrylamide, as well as esters, acids and nitriles containing an acrylyl moiety, with methyl acrylate being the preferred coreactant material. In general other preferred unsaturated reactants are volatile or otherwise readily removed from the core/coreactant reaction products without deleteriously affecting the reaction product.

Examples of the second coreactant materials used to react with the adduct of the nucleophilic core and the first coreactant include various polyamines such as alkylene polyamines and polyalkylene polyamines such as ethylenediamine and diethylenetriamine; benzylic polyamines such as tris(1,3,5-aminomethyl)benzene; alkanolamines such as ethanolamine; and aziridine and derivatives thereof such as N-aminoethyl aziridine. Of these second coreactant materials, the volatile polyamines such as ethylenediamine and diethylenetriamine are preferred, with ethylenediamine being especially preferred.

Alternatively, the dendrimers can be prepared by reacting an electrophilic core such as a polyester with a coreactant such as a polyamine to form a core adduct which is then reacted with a suitable second coreactant such as an unsaturated ester to form the first generation product. Thereafter, this first generation product is reacted with a suitable third coreactant such as polyamine and then with the second coreactant such as unsaturated ester to form the desired second generation dendrimer. Examples of suitable electrophilic cores include the $C_1$–$C_4$ alkyl esters of various polycarboxylic acids such as benzene tricarboxylic acid, oxalic acid, terphthalic acid and various other carboxylic acids represented by the formula:

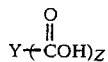

wherein Y is hydrocarbyl or a hydrocarbon polyl wherein the hydrocarbon radical is alkyl, aryl, cycloalkyl, alkylene, arylene, cycloalkylene, and corresponding trivalent, tetravalent, pentavalent and hexavalent radicals of such hydrocarbons; and Z is a whole number from 1 to 6. Preferred electrophilic cores include poly(methyl acrylates), poly(acryloyl chloride), poly(methacryloyl chloride), alkyl acrylate/alkyl methacrylate copolymers, polymers of alkyl fumarates, and polymers of alkyl itaconates. Of the electrophilic cores, alkyl acrylate/alkyl methacrylate copolymers and alkyl acrylate/alkyl itaconate copolymers are most preferred.

Suitable first coreactants for reaction with the electrophilic core include polyalkylene polyamines such as ethylenediamine, diethylenetriamine, triethylenetetramine and other polyamines represented by the formula:

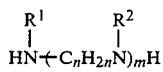

wherein $R^1$ and $R^2$ independently represent hydrogen or an alkyl, preferably $C_1$-$C_4$ alkyl, hydroxyalkyl, cyanoalkyl, or amido; n is at least 2 and preferably 2 to 6 and m is 2 to 100, preferably 2 to 5. Examples of suitable second coreactants to be used in preparing dendrimers from electrophilic cores include alkyl esters of ethylenically unsaturated carboxylic acids such as methyl acrylate, methyl methacrylate, ethyl acrylate and the like. Examples of suitable third coreactants are those illustrated for the first coreactant.

Thus prepared, the dendrimers can be reacted with a wide variety of compounds to produce the polyfunctional compounds having the unique characteristics that are attributable to the structure of the dendrimer. For example, a dendrimer having terminal amine moieties, as in the polyamidoamine dendrimer, may be reacted with an unsaturated nitrile to yield a polynitrile (nitrile-terminated) dendrimer. Alternatively, the polyamidoamine dendrimer may be reacted with (1) an $\alpha,\beta$-ethylenically unsaturated amide to form a polyamide (amide-terminated) dendrimer, (2) an $\alpha,\beta$-ethylenically unsaturated ester to form a polyester (ester-terminated) dendrimer, (3) an oxirane to yield a polyol (hydroxy-terminated) dendrimer, or (4) an ethylenically unsaturated sulfide to yield a polymercapto (thiol-terminated) dendrimer. In addition, the dendrimer may be reacted with an appropriate difunctional or trifunctional compound such as an alkyl dihalide or an aromatic diisocyanate to form a poly(dendrimer) having a plurality of dendrimers linked together through the residues of the polyhalide or polyisocyanate. In all instances, such derivatives of the dendrimers are prepared using procedures and conditions conventional for carrying out reactions of organic compounds bearing the particular functional group with the particular organic reactant.

Such reactions are further exemplified by the following working examples. In such working examples, all parts and percentages are by weight unless otherwise indicated.

EXAMPLE 1

A. Preparation of Core Adduct

To a one-liter, 3-neck flask equipped with stirrer, condenser and thermowell, and containing methyl acrylate (296.5 g, 3.45 moles) is added at room temperature with stirring over a 6-hour period ammonia (8.7 g, 0.58 mole) dissolved in 102.2 g of methanol. The mixture is allowed to stand at room temperature for 48 hours at which point excess methyl acrylate is removed by vacuum distillation (1 mm Hg at 22° C.) yielding 156 g of residue. This residue is analyzed by size exclusion chromatography ($C_{13}$ NMR) and liquid chromatography. This analysis indicates the coreactant adduct to be the Michael's addition product of 1 mole of ammonia and 3 moles of methyl acrylate at a 97.8 percent yield.

B. Preparation of First Generation Adduct

To ethylenediamine (505.8 g, 8.43 moles) dissolved in 215.4 g of methanol in a 3-liter reaction flask equipped with stirrer, condenser and thermowell, is added the aforementioned ammonia/methyl acrylate adduct (28.1 g, 0.1022 mole), and the reaction mixture is allowed to stand at room temperature for 55 hours. The resulting mixture (747.6 g) is subjected to vacuum distillation to remove excess ethylenediamine and methanol at 2 mm Hg and 72° C. The residue (35.4 g) is analyzed by size exclusion chromatography and other suitable analytical techniques. The analyses indicate that essentially all of the ester moieties of the ammonia/methyl acrylate adduct had been converted to amides in the form of a compound represented by the following structural formula:

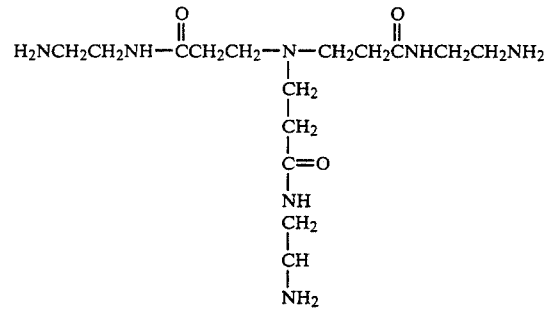

thus indicating a yield of 98.6 percent.

C. Preparation of Second Generation Polyester Dendrimer

To methyl acrylate (93.2 g, 1.084 moles) in a one-liter flask equipped with condenser, stirrer and thermowell, and heated to 32° C. is added the aforementioned first generation adduct (18 g, 0.0501 mole) dissolved in 58.1 g of methanol over 1.5 hours. The resulting mixture is maintained at 32° C. for an additional 5 hours and allowed to stand an additional 18 hours at room temperature. The reaction mixture (165.7 g) is stripped of methanol and excess methyl acrylate by vacuum distillation (2 mm Hg and 50° C.) to produce 43.1 g of residue. Analysis by suitable techniques indicates the product to be a second generation polyester dendrimer represented by the following formula:

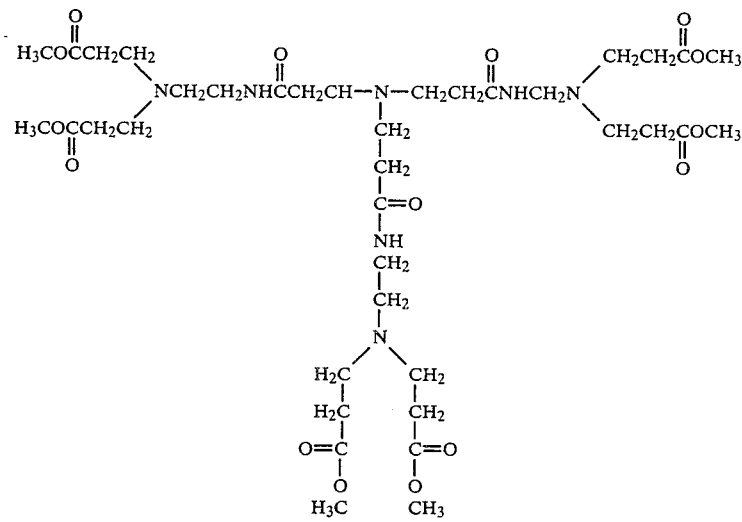

in 98.4 percent yield.

D. Preparation of Second Generation Polyamine Dendrimer

To ethylenediamine (328.8 g, 5.48 moles) dissolved in 210.2 g of methanol at room temperature in the aforementioned flask is added with stirring the second generation polyester dendrimer (34.9 g, 0.0398 mole) dissolved in 45.3 g of methanol. The resulting mixture is allowed to stand for 66 hours at room temperature at which time excess ethylenediamine and methanol is stripped from the product by vacuum distillation (2 mm Hg at 72° C.) to yield 41.1 g (99.0 percent yield) of product. This product is determined by size exclusion chromatography to be the second generation polyamine of the aforementioned polyester dendrimer.

E. Preparation of Third Generation Polyester Dendrimer

To methyl acrylate (65.1 g, 0.757 mole) is added the aforementioned second generation polyamine dendrimer (28.4 g, 0.0272 mole) dissolved in 84.6 g of methanol over a period of 1 hour and 15 minutes. The resulting mixture is allowed to stand for 18 hours at 25° C. after which time excess methyl acrylate and methanol are removed by vacuum distillation (2 mm Hg at 50° C.) to yield 56.3 g (100.0 percent yield) of product residue. Analysis of this residue by suitable analytical techniques indicate that it is a third generation polyester dendrimer having 3 core branches with 4 terminal ester moieties per core branch thereby providing 12 terminal ester moieties per dendrimer molecule.

F. Preparation of Third Generation Polyamine Dendrimer

To ethylenediamine (437.6 g, 7.29 moles) dissolved in 192 g of methanol is added the aforementioned third generation polyester dendrimer (44.9 g, 0.0216 mole) dissolved in 69.7 g of methanol. The addition occurs over a period of 48 hours at 25° C. with stirring. The resulting reaction mixture is then allowed to stand for 19 hours at 25° C. after which time excess methanol and ethylenediamine are removed by vacuum distillation (2 mm Hg at 72° C.) to yield 51.2 g of residual product. Analysis of this residue indicates a yield of 85.3 percent of a third generation polyamine dendrimer having 3 core branches with 4 terminal primary amine moieties per core branch, thereby providing 12 terminal primary amine moieties per molecule of dendrimer. This dendrimer is calculated to have a molecular volume of 50,000 to 97,000 cubic Å and a density of a terminal amine moiety of 1 to 3($\times 10^{-4}$) moieties/cubic Å.

EXAMPLE 2

Following the procedure of Example 1, except that a molar equivalent amount of ethylenediamine is substituted for ammonia as the core compound, a third generation polyamine dendrimer is prepared. Upon analysis, it is determined that this dendrimer has four core branches with 4 terminal primary amine moieties per core branch, thereby providing 16 terminal primary amine moieties per molecule of dendrimer. This dendrimer has a molecular volume of 60,000 to 120,000 cubic Å and a terminal amine density of 2 to 6($\times 10^{-4}$) amines/cubic Å.

Similar dendrimers are obtained when equimolar amounts of 1,2-diaminopropane, 1,3-diaminopropane and 1,6-diaminohexane (hexamethylenediamine) are substituted for the ethylenediamine as the core compound in the foregoing procedure. When an equimolar amount of dodecylamine or benzylamine is substituted for the ethylenediamine as the core compound, the resulting dense star polymers have 2 core branches per molecule with 4 terminal primary amine groups per branch, thereby providing a total of 8 primary amine groups per polymer molecule. Substitution of triaminoethylamine for ethylenediamine as the core compound yields a dendrimer having 6 core branches with 4 terminal primary amine moieties per core branch, thereby providing 24 terminal primary amine moieties per molecule of dendrimer.

EXAMPLE 3

A. First Amidation

Following the procedure of Example 1, 5 g (0.0198 mole) of trimethyl-1,3,5-benzenetricarboxylate is mixed with 6.3 g (0.0368 mole) of aminoethylethanolamine ($NH_2CH_2CH_2NHCH_2CH_2OH$) to form a white paste. This mixture is heated at 120° C. for 3 hours to form 9.48 g of a light yellow syrup which infrared and nuclear magnetic resonance spectral analysis indicate is an amidoamine represented by the structural formula:

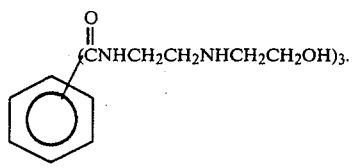

1,3,5-isomer

B. First Alkylation

A 9.48 g (0.0202 mole) of this amidoamine is combined with a stoichiometric excess (11.0 g, 0.127 mole) of methyl acrylate and heated for 24 hours at 80° C. which, after devolatilization, is a light yellow syrup weighing 14.66 g. Nuclear magnetic resonance ($H^1$) and infrared spectral analysis of the syrup indicates that it is a triester represented by the structural formula:

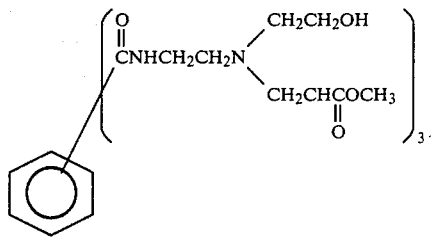

1,3,5-isomer

C. Second Amidation

Following the procedure of part A of this example, the triester (4.57 g, $6.3 \times 10^{-3}$ mole) produced in part B is mixed with 1.96 g ($1.89 \times 10^{-2}$ mole) of aminoethylethanolamine and heated at 90° C. for 48 hours to form 5.8 g of a light yellow, highly viscous syrup. Analysis of this product by nuclear magnetic resonance ($H^1$) (DMSO-$d_6$) and infrared spectroscopy indicates that it is a triamidoamine represented by the structural formula:

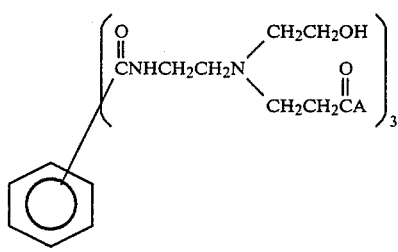

wherein each A is individually

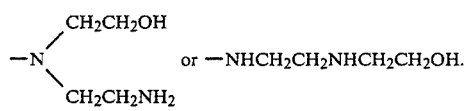

EXAMPLE 4

A. First Amidation

A 27.3-g portion (0.1 mole) of a triester represented by the formula:

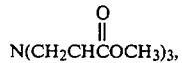

is mixed with 30 g (0.405 mole) of N-methyl ethylenediamine (MEDA) and 16.6 g of methanol and then heated at 63° C. for 11 hours. The product is then stripped of unreacted MEDA and methanol to yield 36.1 g of a triamide represented by the formula:

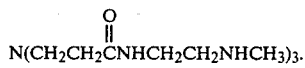

B. First Alkylation

To the aforementioned triamide (36.1 g, 0.09 mole) is added 38.5 g of methanol to yield a clear solution to which is added 50.5 g (0.59 mole) of methyl acrylate dropwise over a period of 2 hours at 38° C. The temperature of the resulting mixture is increased to 53° C. for 5 additional hours after which unreacted methyl acrylate and methanol are removed under vacuum to yield 61 g of a light yellow syrup. Analysis of this product by nuclear magnetic resonance ($H^1$) spectroscopy indicates that it is represented by the formula:

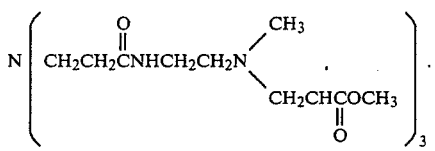

C. Second Amidation

To 60.8 g of the aforementioned first alkylation product are added with stirring 42.7 g of methanol and 26.6 g (0.359 mole) of MEDA followed by heating the resulting mixture at 65° C. for 6 hours. Vacuum stripping of the mixture yields 72.7 g of a light yellow syrup. Analysis of this product (syrup) indicates that it is a mixture of isomers having the following structures:

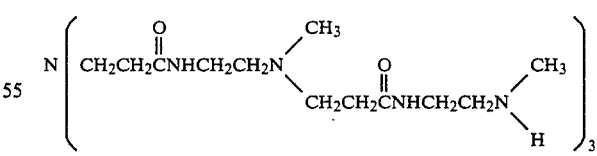

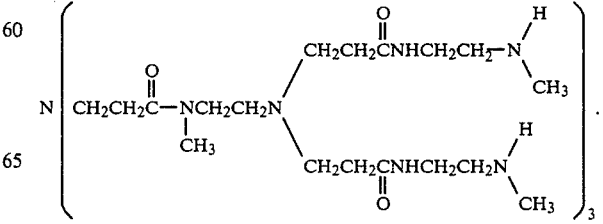

D. Second Alkylation and Third Amidation

Alkylation of the aforementioned second amidation product with methyl acrylate and then amidation of the resulting alkylated product with MEDA in accordance with aforementioned procedures yield a mixture of isomers having core branches with dendritic characteristics.

What is claimed is:

1. A dense star polymer having at least one core branch emanating from a core, each core branch having at least one terminal group and amidoamine linkages provided that (1) the ratio of terminal groups to the branches emanating from the core is two or greater, (2) the density of terminal groups in the polymer is at least 1.5 times that of a conventional star polymer having a comparable molecular weight and number of core branches, each of such branches of the conventional star polymer bearing only one terminal group, and (3) a molecular volume that is no greater than 60 percent of the molecular volume of said conventional star polymer.

2. The dense star polymer of claim 1 having (1) at least 2 core branches per core, (2) a terminal group density at least 5 times that of the corresponding conventional star polymer, and (3) a molecular volume that is equal to or less than 50 percent of the volume of the conventional star polymer.

3. A dendrimer having a polyvalent core that is covalently bonded to at least 1 ordered dendritic branch which extends to two generations such that each dendritic branch has at least four terminal groups and a symmetrical structure.

4. The polymer of claim 1 wherein the dendritic branches contain amidoamine linkages.

5. The polymer of claim 1 wherein the core is derived from a nucleophilic compound and the branches are polyamidoamines wherein the terminal groups are primary amine groups.

6. The polymer of claim 1 wherein the core is derived from a nucleophilic compound having a plurality of active hydrogens capable of undergoing a Michael's addition reaction with an ethylenically unsaturated group.

7. The polymer of claim 5 wherein (1) the nucleophilic compound has a plurality of active hydrogens capable of undergoing a Michael's addition reaction with an ethylenically unsaturated group and (2) the branches are polyamidoamine which is derived from the reaction of an alkyl ester of an α,β-ethylenically unsaturated carboxylic acid or an α,β-ethylenically unsaturated amide and an alkylene polyamine or a polyalkylene polyamine.

8. The polymer of claim 7 wherein the nucleophilic compound is ammonia, the ester is methyl acrylate and the alkylene polyamine is ethylenediamine.

9. The polymer of claim 1 which is represented by the formula:

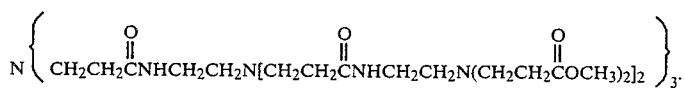

10. A dendrimer having (1) a polyvalent core derived from a nucleophilic compound selected from the group consisting of ammonia and (2) at least two ordered dendritic polyamidoamine core branches which (a) are covalently bonded to the polyvalent core, (b) extend through at least two generations, and (c) have at least 3 terminal groups per core branch.

11. The dendrimer of claim 10 wherein (1) the dendritic core branches are derived from (a) methyl acrylate, ethyl acrylate, acrylamide or maleic anhydride and (b) a polyamine, an alkanolamine or an aziridine and (2) there are from 4 to 1024 terminal groups per core branch.

12. The dendrimer of claim 11 wherein (1) the core is derived from ammonia or a polyalkylene polyamine and (2) the core branch is derived from methyl acrylate and ethylenediamine or diethylenetriamine.

13. The dense star polymer of claim 2 having at least 3 core branches per core.

14. A polymer which is represented by the formula:

* * * * *

UNITED STATES PATENT AND TRADEMARK OFFICE
CERTIFICATE OF CORRECTION

PATENT NO. : 4,507,466

DATED : March 26, 1985

INVENTOR(S) : Donald A. Tomalia and James R. Dewald

It is certified that error appears in the above-identified patent and that said Letters Patent is hereby corrected as shown below:

Title page, column 1, line 5 should read -- Assignee: The Dow Chemical Company --.

Column 1, line 19, the word "to" should read -- in --.

Column 2, line 55, the word "in" should read -- is --.

Column 3, line 1, "configuration." should read -- configuration: --.

Column 4, line 58, "1:33:1" should read --1.33:1--.

Column 5, line 5, the dendritic branch bonding the two N's together was omitted in both formulas. It should read:  

Column 5, line 51, "$N_4$" should read -- $N_r$ --.

UNITED STATES PATENT AND TRADEMARK OFFICE
CERTIFICATE OF CORRECTION

PATENT NO. : 4,507,466

DATED : March 26, 1985

INVENTOR(S) : Donald A. Tomalia and James R. Dewald

It is certified that error appears in the above-identified patent and that said Letters Patent is hereby corrected as shown below:

Column 5, lines 55-65, the formula shown should be correctly pictured as follows:

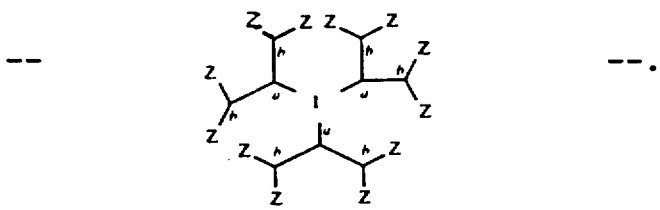

Column 6, line 34, the word "of" should read -- or --.

Column 8, line 2, the word "dimercaptoethylene" should read --dimercaptoethane--.

Signed and Sealed this

Tenth Day of September 1985

[SEAL]

Attest:

DONALD J. QUIGG

Attesting Officer    Acting Commissioner of Patents and Trademarks - Designate